United States Patent
Ziv et al.

(10) Patent No.: US 7,828,713 B2
(45) Date of Patent: Nov. 9, 2010

(54) GASTROINTESTINAL DEVICE

(76) Inventors: Yehiel Ziv, 2280 Street, Apt. 1, Tel Aviv, 69086 (IL); Avinoam Nevler, 4 Philadelphia Street, Tel Aviv, 69183 (IL); Alon Nahshon, 332 HaAtzma'ut Street, Zichron Yaakov, 30900 (IL); Vladimir Ryabtsev, 12 HaNotrim Street, Apt. 1, Herzliya, 46449 (IL); Meir Gitelis, Moshav Bnei Atarot, 60991 (IL)

( * ) Notice: Subject to any disclaimer, the term of this patent is extended or adjusted under 35 U.S.C. 154(b) by 837 days.

(21) Appl. No.: 10/585,115

(22) PCT Filed: Jan. 2, 2005

(86) PCT No.: PCT/IL2005/000002
§ 371 (c)(1), (2), (4) Date: Jun. 30, 2006

(87) PCT Pub. No.: WO2005/065575
PCT Pub. Date: Jul. 21, 2005

(65) Prior Publication Data
US 2008/0294257 A1    Nov. 27, 2008

Related U.S. Application Data

(60) Provisional application No. 60/534,196, filed on Jan. 2, 2004.

(51) Int. Cl.
*A61F 2/00* (2006.01)
(52) U.S. Cl. ...................................... 600/29
(58) Field of Classification Search ............ 600/29–32, 600/37; 128/897, 899; 604/19, 27, 30–34

See application file for complete search history.

(56) References Cited

U.S. PATENT DOCUMENTS

| 4,967,844 | A  | * | 11/1990 | Brooks et al. ............... 166/381 |
| 5,593,443 | A  |   | 1/1997  | Carter et al. |
| 6,432,040 | B1 | * | 8/2002  | Meah .......................... 600/37 |
| 6,638,208 | B1 |   | 10/2003 | Natarajan et al. |
| 6,752,754 | B1 | * | 6/2004  | Feng et al. ..................... 600/30 |
| 2003/0032857 | A1 |   | 2/2003 | Forsell |
| 2004/0092892 | A1 | * | 5/2004 | Kagan et al. ................. 604/264 |
| 2004/0147801 | A1 | * | 7/2004 | Kugler et al. ................. 600/12 |

FOREIGN PATENT DOCUMENTS

| WO | WO 00/02499   | 1/2000  |
| WO | WO 01/54615   | 8/2001  |
| WO | WO 2004/106782 | 12/2004 |

* cited by examiner

*Primary Examiner*—Charles A Marmor, II
*Assistant Examiner*—Christine D Hopkins
(74) *Attorney, Agent, or Firm*—Dekel Patent Ltd; David Klein

(57) ABSTRACT

A gastrointestinal device including a casing including fixation elements adapted for intraluminal fixation of the device in a gastrointestinal tract (e.g., the anorectal wall), a valve disposed in the casing and controllable to move from a closed position, which significantly restricts passage of gastrointestinal (e.g., fecal) matter therepast, and an open position, which permits passage of gastrointestinal matter therepast, and a controller operatively connected to the valve for externally controlling the position of the valve between the closed and open positions.

15 Claims, 12 Drawing Sheets

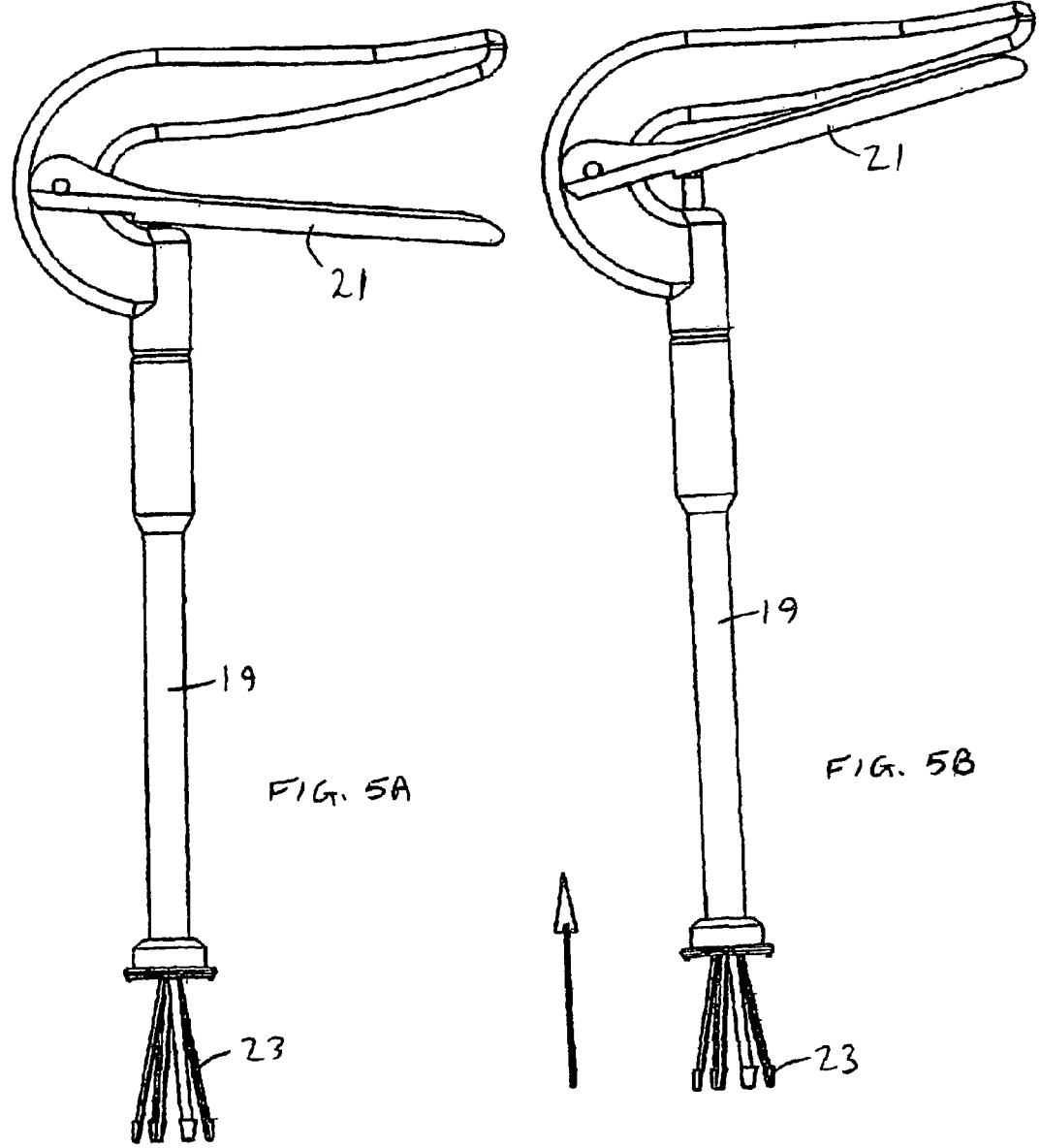

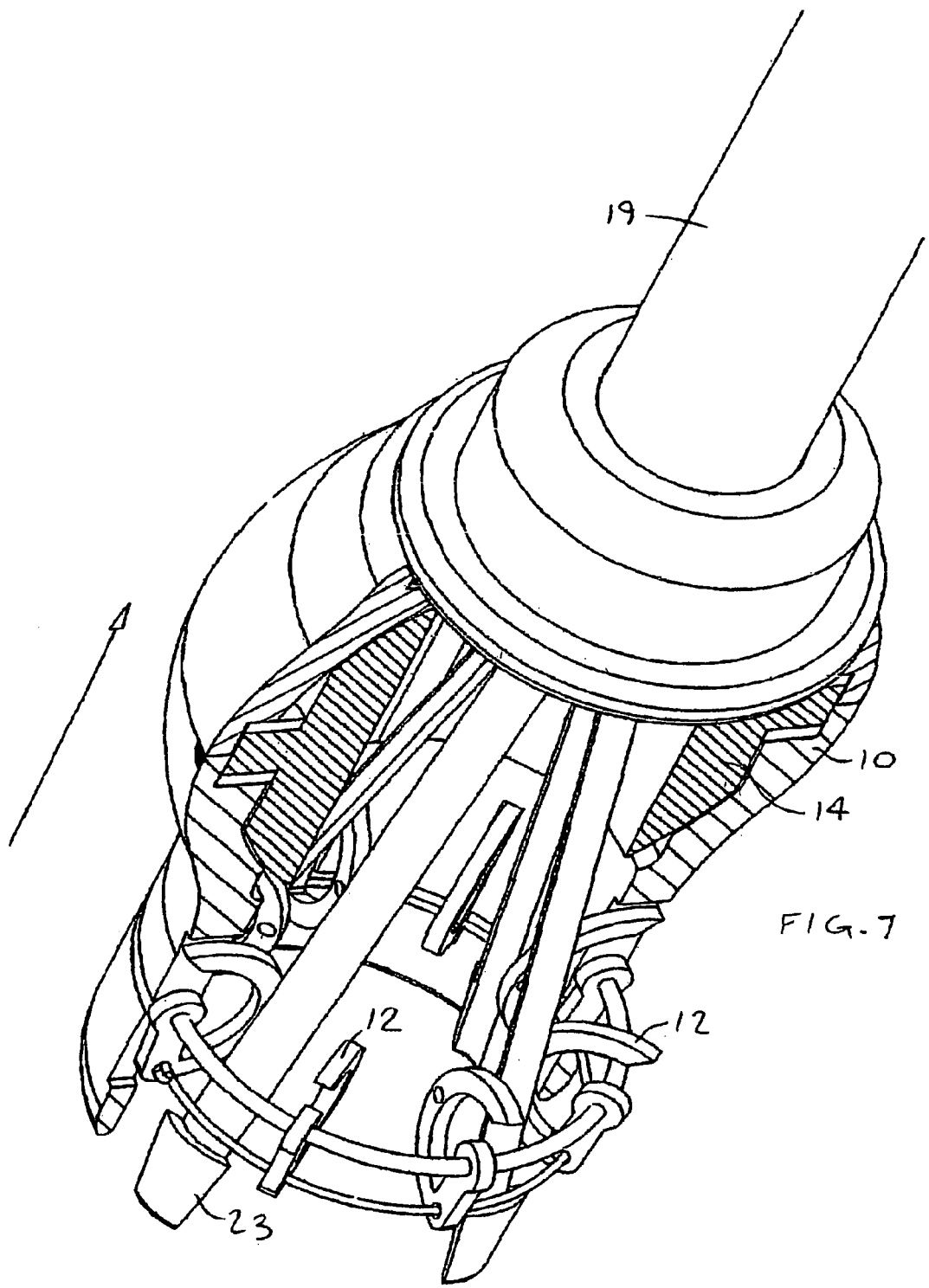

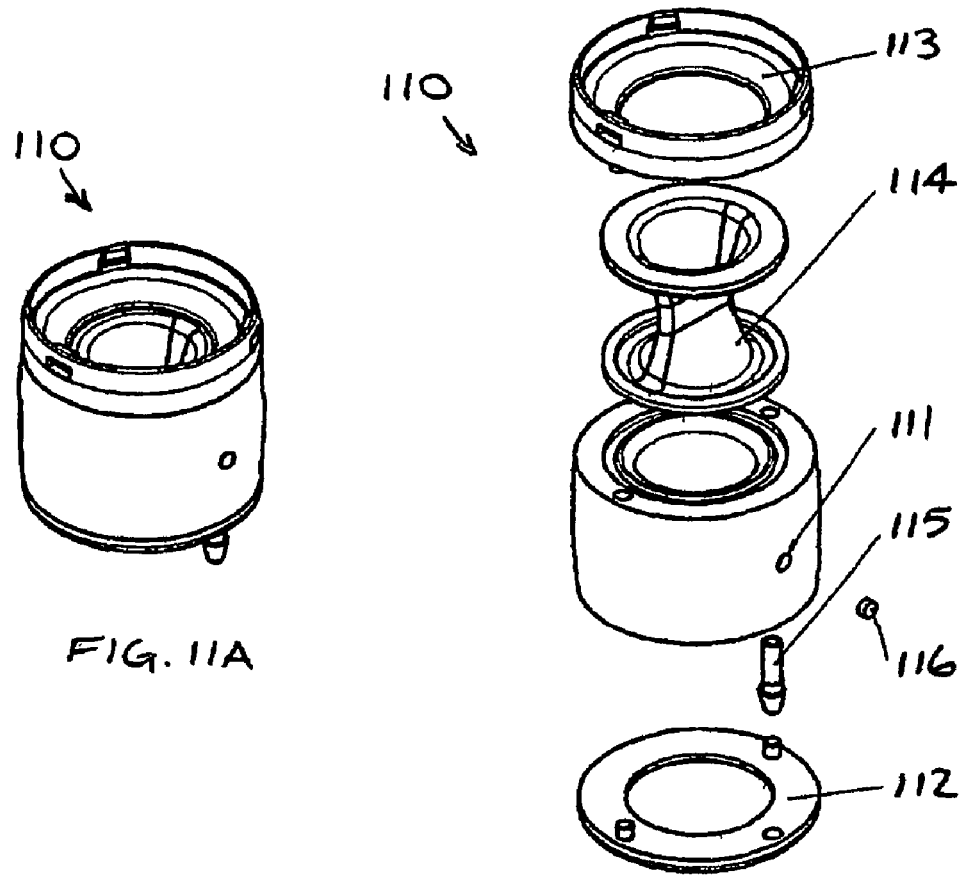
FIG. 11A
FIG. 11B
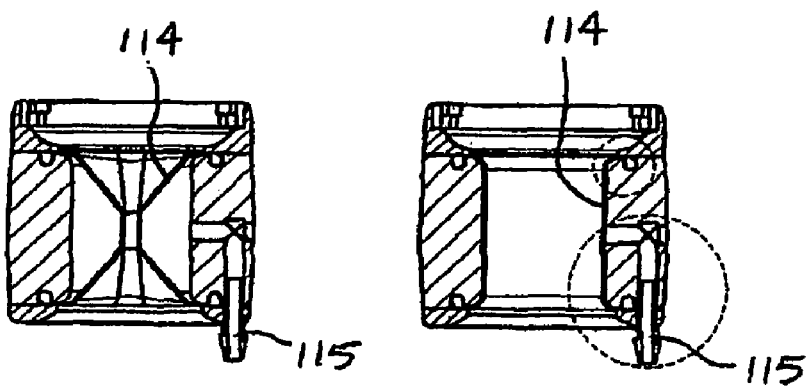
FIG. 11D
FIG. 11C

GASTROINTESTINAL DEVICE

CROSS-REFERENCE TO RELATED APPLICATIONS

This application claims priority under 35 USC §119 to U.S. Provisional Patent Application Ser. No. 60/534,196, filed Jan. 2, 2004.

FIELD OF THE INVENTION

The present invention relates generally to gastrointestinal devices, such as apparatus for controlling fecal incontinence.

BACKGROUND OF THE INVENTION

Fecal incontinence is a common, under-diagnosed, medical affliction. Approximately 1 in 15 of the adult population may develop some degree of fecal incontinence. Its prevalence in the general population ranges between 2.2-6.9% and in the United States alone it involves 5.5 to 17 million people. 30% of the people are over 60 years old, and over 63% are women. The economic impact of incontinence treatment amounts to 16-26 billion USD annually.

The degree of fecal incontinence can be classified into 4 grades: 0—Competent, 1—Gas Incontinence, 2—Soiling and grade 3—Complete (solid content) incontinence.

The causes of chronic incontinence are various and can be divided into 6 main subgroups: 1) Traumatic/Surgical, 2) Inflammatory, 3) Neurology, 4) Psychiatric, 5) Congenital, and 6) Miscellaneous.

Traumatic etiology is the main cause of fecal incontinence. Obstetric trauma and even uncomplicated vaginal deliveries have been found to be a key factor in the development of incontinence in adult women. Other traumatic causes include mechanic trauma, iatrogenic trauma, surgical resection and irradiation. In the inflammatory subgroup of patients with incontinence, the inflammatory bowel diseases (i.e. ulcerative colitis and Crohn's Disease) account for most of the cases. The neurological subgroup includes patients with incontinence due to CVA, multiple sclerosis, spinal cord injury and other autonomic and motor disorders. While advances have been made in the field of urinary incontinence treatment, the management modalities of fecal incontinence offer a very small selection: change of lifestyle, change of diet, experimental use of surgically implantable mechanic sphincter, experimental use of surgically implantable electrical muscle stimulator, and/or experimental surgical sphincter reconstruction.

Change of lifestyle and change of diet (bulk forming) are the first steps generally taken by patients having fecal incontinence.

The implantable mechanic sphincter is a variation of an older urinary sphincter. The device, ring shaped, is surgically inserted around the rectum and is hydraulically inflated/deflated to control the passage.

The implantable electrical muscle stimulator may assist in the treatment of light to moderate fecal incontinence and requires an intact muscular structure of the sphincter.

The surgical reconstruction consists of detaching the distal ends of the gracilis muscles in the legs and overlapping those ends around the rectum to create a new muscular sphincter. The operation usually continues with insertion of an electronic muscle stimulator for the reconstructed sphincter.

SUMMARY OF THE INVENTION

The present invention seeks to provide a novel gastrointestinal device, which may be used for controlling fecal incontinence, as is described in detail hereinbelow.

It is noted that the gastrointestinal device of the present invention is described hereinbelow for use as a device attached to the anorectal wall to control or treat fecal incontinence. However, the invention is not limited to this application and the invention may be used in other parts of the gastrointestinal tract as well as other lumens in the body.

The present invention may include an intra-lumen, patient controlled and easily inserted device. The device itself (artificial sphincter), the insertion process, separation process and the fixation method of the device are all new innovations in the management of patients with fecal incontinence.

BRIEF DESCRIPTION OF THE DRAWINGS

The present invention will be understood and appreciated more fully from the following detailed description taken in conjunction with the drawings in which:

FIGS. 4, 5A, 5B, 6A and 6B are simplified pictorial illustrations of an insertion assist device for inserting the gastrointestinal device of FIG. 1 in a rectum;

FIG. 7 is a simplified pictorial, partially cutaway illustration of the insertion assist device being used to rotate fixation hooks of the gastrointestinal device of FIG. 1;

FIGS. 11A and 11B are simplified pictorial and exploded views, respectively, of a gastrointestinal device, constructed and operative in accordance with another embodiment of the present invention, including a flexible sleeve and a fluid inlet;

FIGS. 11C and 11D are simplified sectional illustrations of the gastrointestinal device of FIGS. 11A and 11B in respective open and closed positions;

DETAILED DESCRIPTION OF EMBODIMENTS

Figure 1:
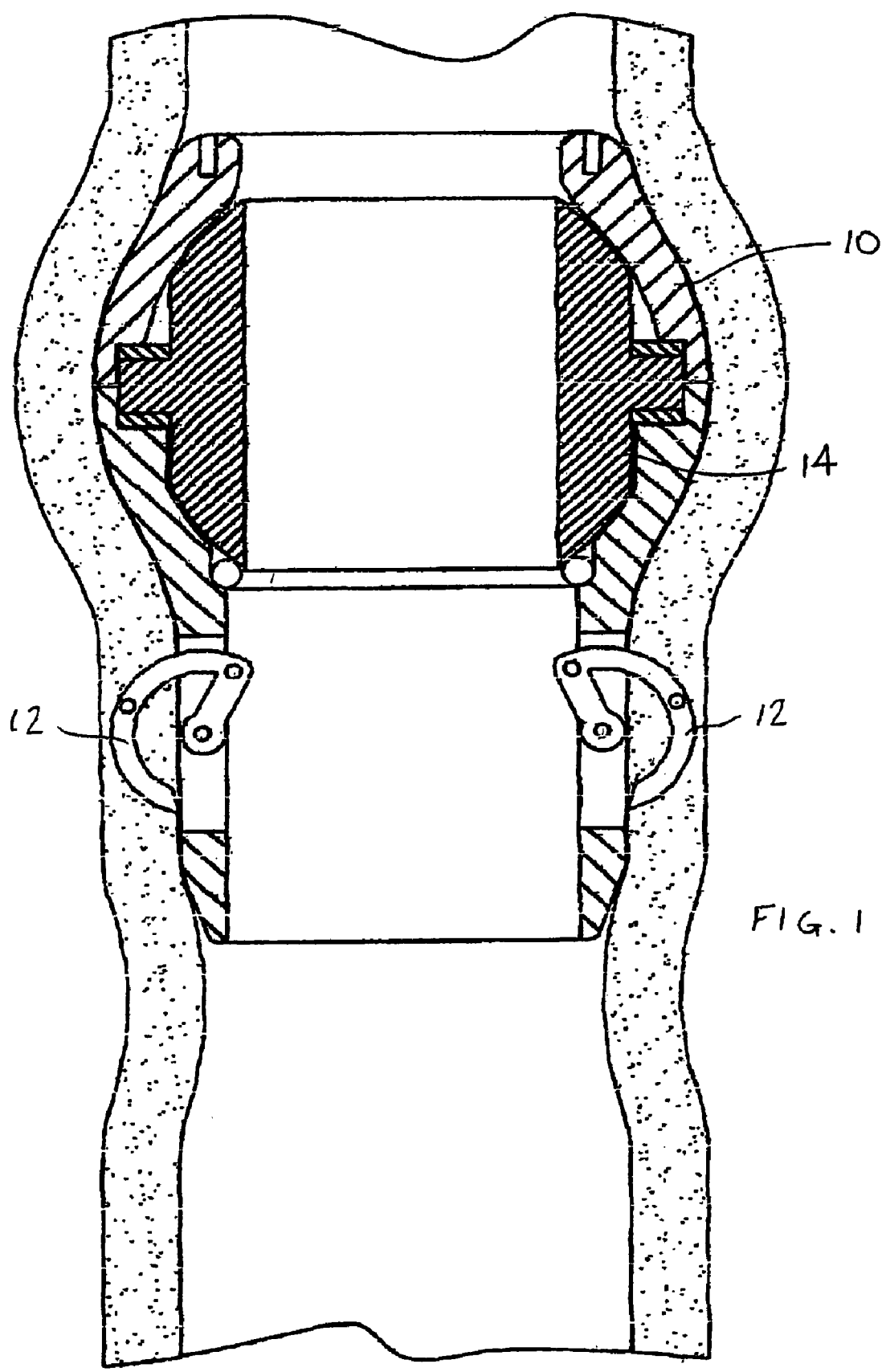
FIG. 1 is a simplified sectional illustration of a gastrointestinal device, constructed and operative in accordance with an embodiment of the present invention, in a deployed, extended configuration.
Figure 2:
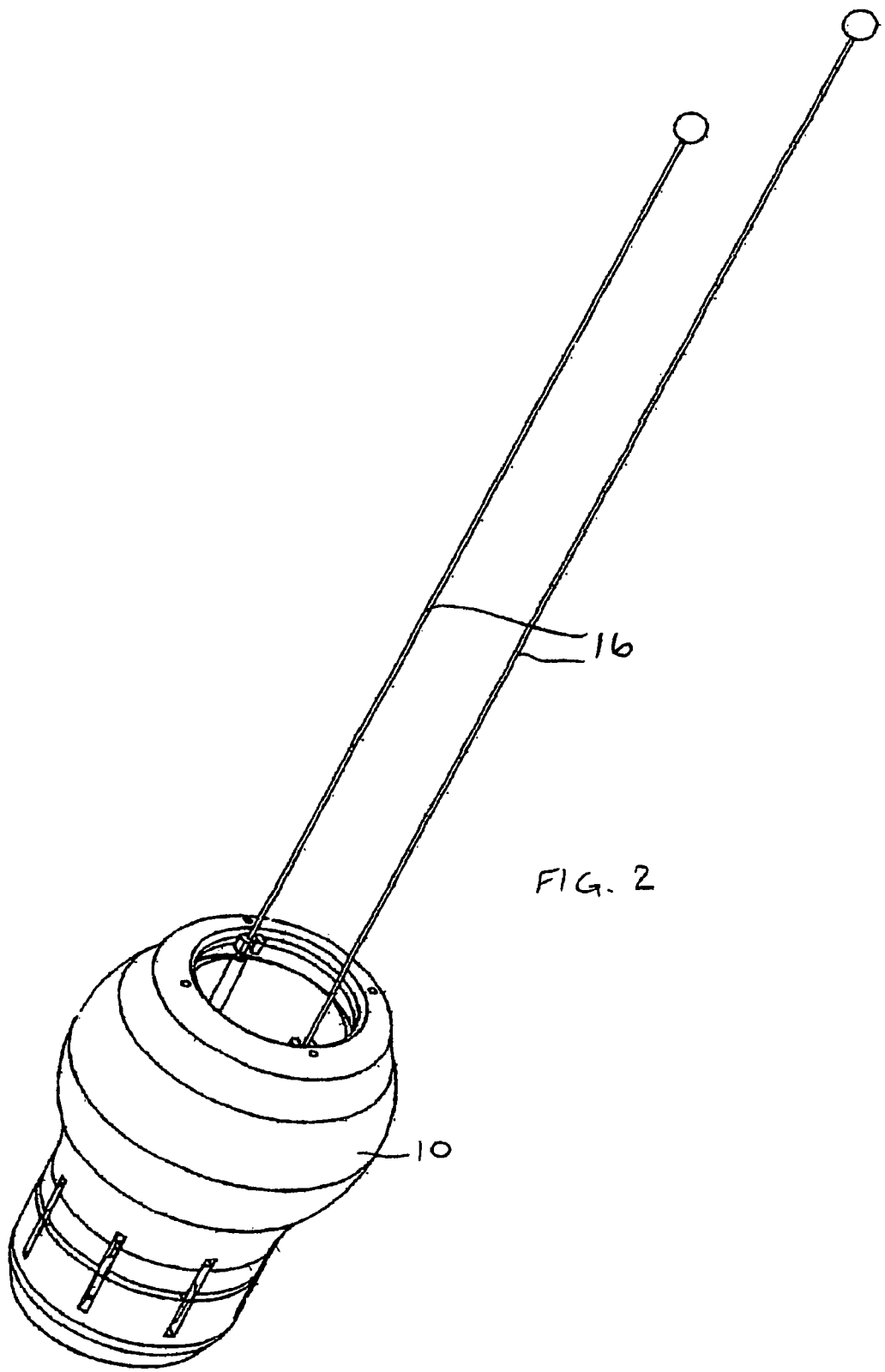
FIG. 2 is a simplified pictorial illustration of the gastrointestinal device of FIG. 1, showing strings which may be pulled to operate the apparatus.
Figure 3:
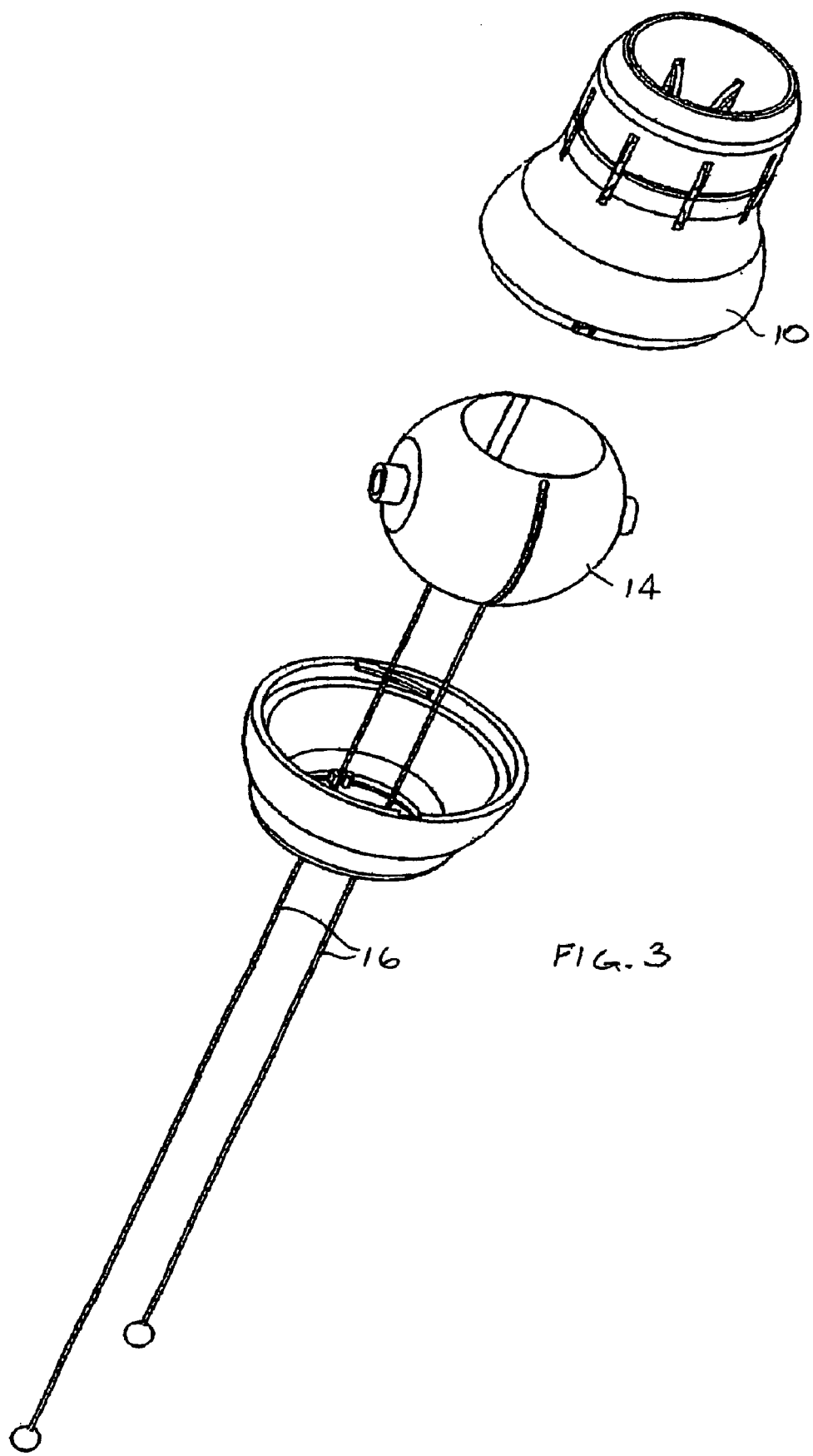
FIG. 3 is a simplified exploded illustration of the device of FIG. 1.
Figure 4:
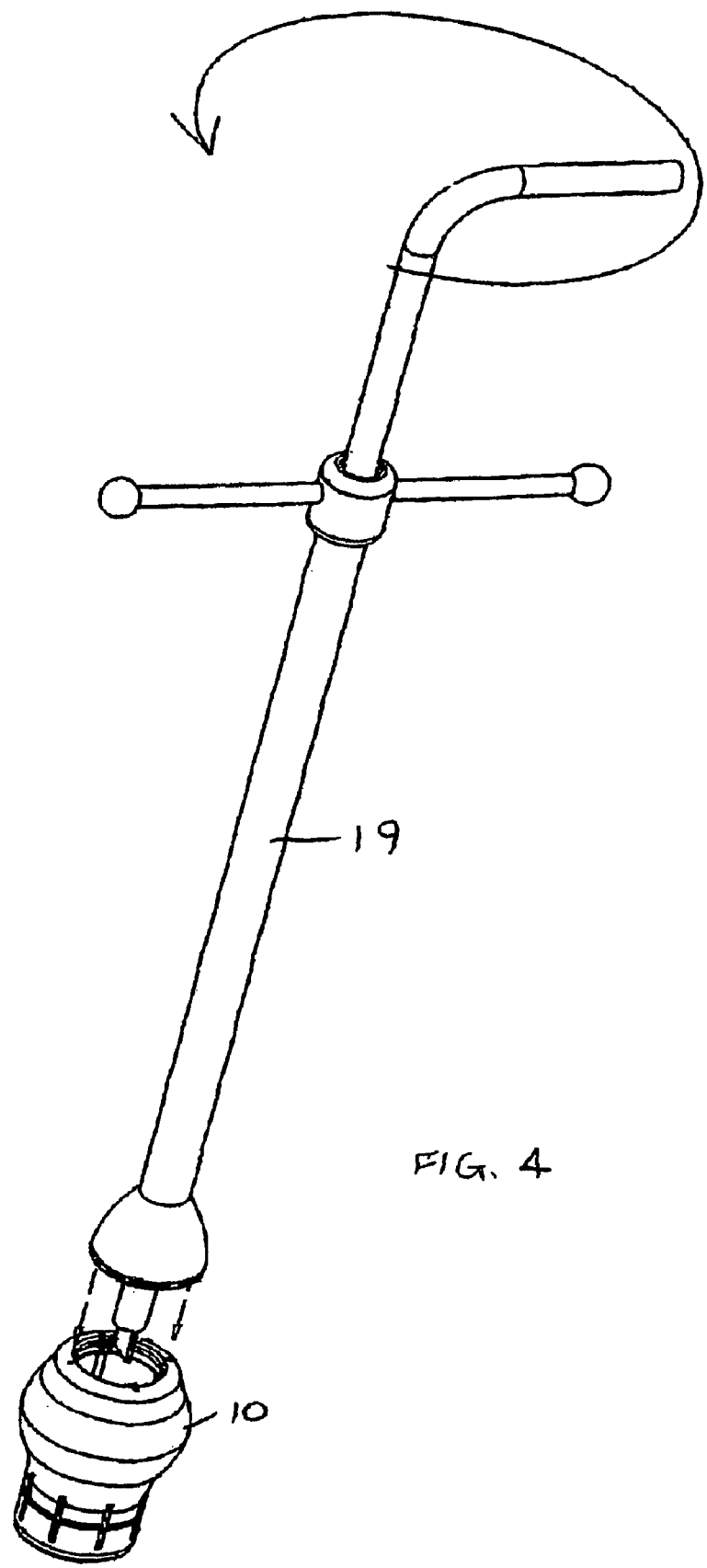
Figure 6A:
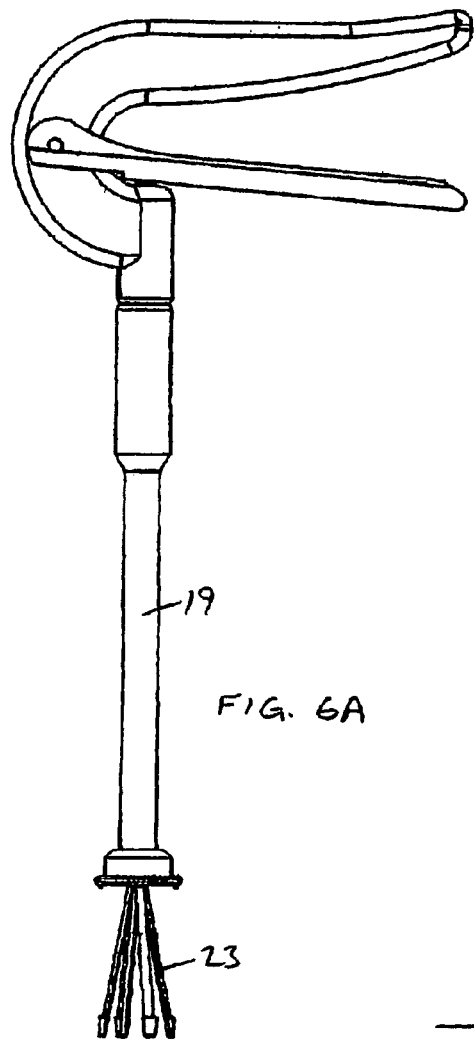
Figure 6B:
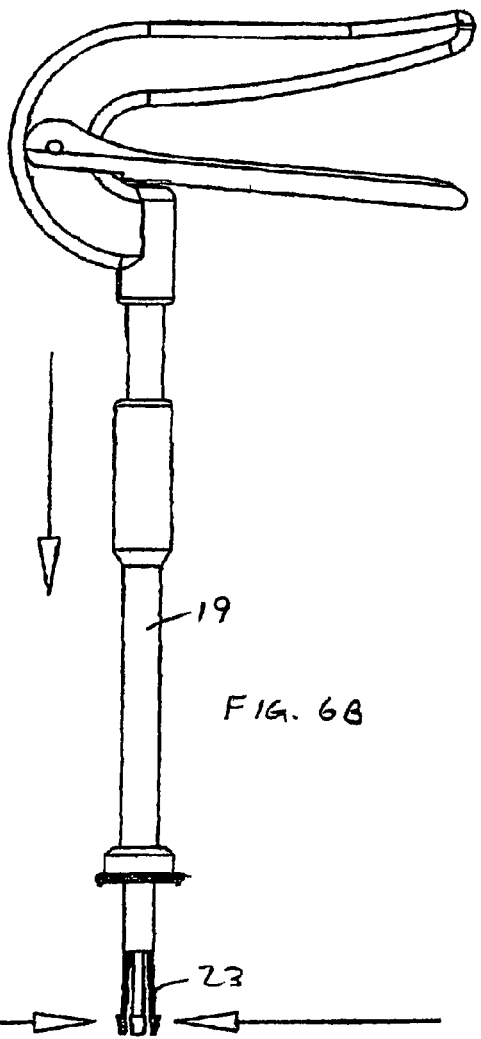

Reference is now made to FIG. 1, which illustrates a gastrointestinal device 8, constructed and operative in accordance with an embodiment of the present invention. The device 8 may be made of an inert FDA approved polymer and may have titanium hooks to anchor it to the anorectal wall.

The device structure may comprise an external bulb-shaped casing 10 in which the narrow end contains fixation elements, such as fixation hooks 12 (e.g., made of titanium), for intraluminal fixation of the device to the anorectal wall. The casing itself can be unscrewed into two pieces enabling the change of the internal mechanism into a new one in the case of failure, without the need for re-operation. The separation of those two pieces may be accomplished by a special cross-shaped device.

The device structure may further comprise an internal ball-valve 14, controlled by a controller which may comprise two strings 16 (e.g., non-absorbable strings) which descend from the device down to the anal orifice, and allow a 90° rotation of the ball in either side. The device may be controlled manually by the patient by pulling the strings, thereby determining the valve status.

The device 8 may be fixed by means of 180° curved titanium hooks that enter intra-luminally and return back to lodge themselves into the device while including the anorectal wall. The device 8 may be fixated so that its lower rim may be situated 3 cm (or some other distance) from the anal verge (lowest part of the gastro intestinal tract).

Figure 8:
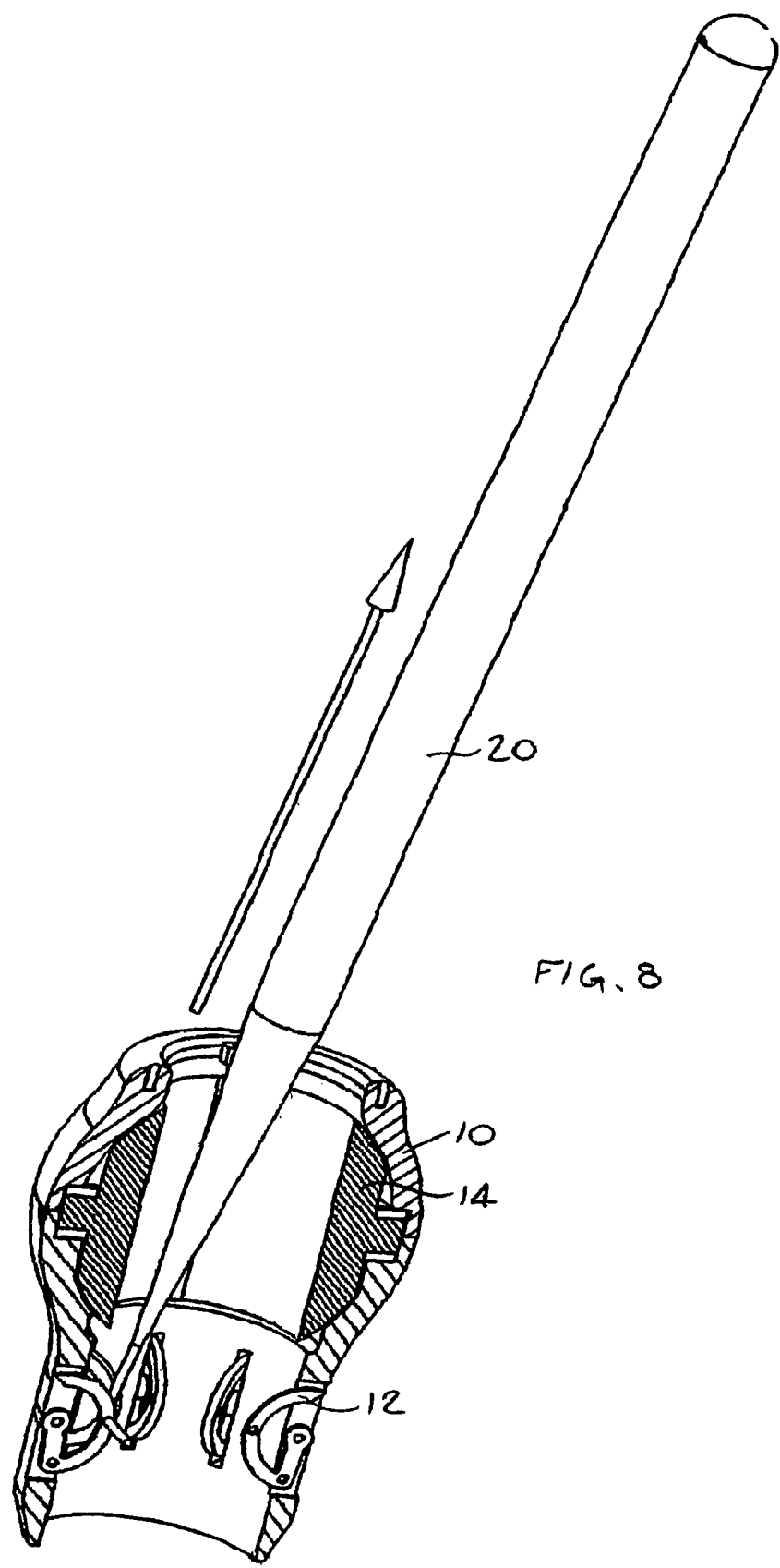
FIG. 8 is a simplified pictorial, partially cutaway illustration of a separation assist device for dislodging the fixation hooks.

The insertion and separation methods of the present invention may be semi-automated by the use of elongated assist devices. The artificial sphincter may be mounted on an insertion assist device 19 and inserted through the anal orifice. A trigger 21 on the assist device 19 simultaneously actuates grabbers 23 that rotate the fixation hooks 12 (see FIG. 7) through the anorectal wall. For separation of the artificial sphincter from the anorectal wall, a similar separation assist device 20 may be provided (FIG. 8). It may be inserted through the anal orifice and the open valve phase of the artificial sphincter, and simultaneously inversely rotates the hooks, thereby detaching the device from the wall.

Both of these methods allow insertion and retrieval of the device without surgical operation and allow the procedure to be performed as an out patient procedure.

The device, assist-devices and the fixation method described above are applicable for any insertion of intraluminal devices. Hence, the internal mechanism of the device may be replaced by other mechanisms for the purposes of one-way valve, intraluminal electronic apparatus, intraluminal sensors, etc. Further examples of different kinds of valves are now described.

Reference is now made to FIGS. 9A-9D, which illustrate a gastrointestinal device 90, constructed and operative in accordance with an embodiment of the present invention.

Gastrointestinal device 90 may include a casing 91 that includes fixation elements (not shown for the sake of simplicity, but may be any of the fixation elements described herein) adapted for fixing the device 90 to the anorectal wall. Casing 91 may be constructed of two halves, but may alternatively have a one-piece construction.

The valve of gastrointestinal device 90 may include a flexible sleeve 92 held at ends thereof by holding members 93. Flexible sleeve 92 is deformable to be open or closed, so as to either permit or restrict passage of gastrointestinal (e.g., fecal) matter therepast. The flexible sleeve 92 may be constructed, without limitation, of a medically safe and compatible fiber (e.g., nylon, DACRON (polyester fiber)) or elastomer or polymeric material, for example. The flexible sleeve 92 may be single-layered or multi-layered (e.g., containing several layers of different elastomers).

A controller may be provided that includes shutters 94 attached to flexible sleeve 92. The shutters 94 may be pivotally mounted on a spherical guide member 95 and may be biased for pivotal movement by biasing devices, such as springs 96. The casing 91 may be closed at ends thereof by closure members 97 and 98.

The shutters 94 may be actuated by strings as above, or by fluid pressure. For example, casing 91 may include a fluid port 99 for connection to a fluid source (not shown, e.g., a source of pressurized water or air, comprising negative or positive pressure) to actuate shutters 94.

Figure 9A:
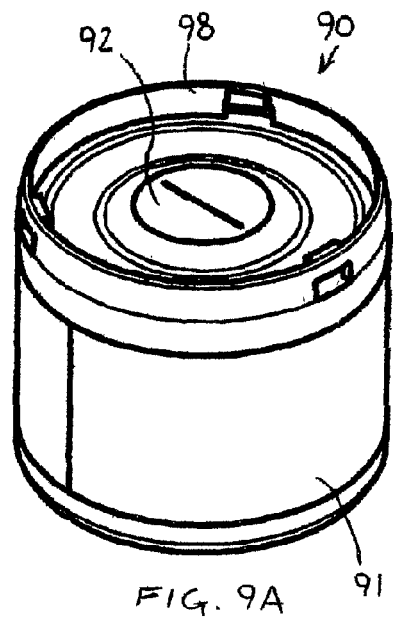
FIGS. 9A and 9B are simplified pictorial and exploded views, respectively, of a gastrointestinal device, constructed and operative in accordance with another embodiment of the present invention, including a flexible sleeve and shutters.
Figure 9B:
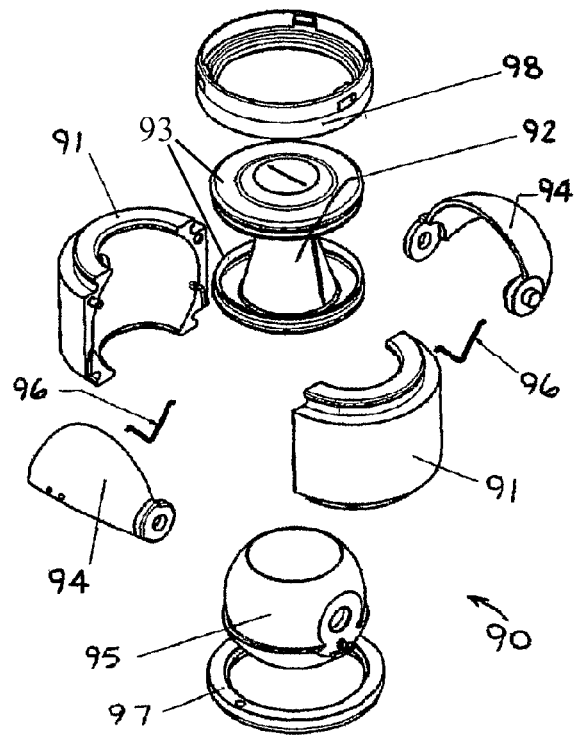
Figure 9C:
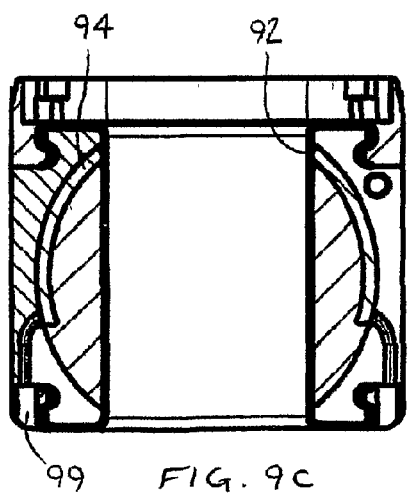
FIGS. 9C and 9D are simplified sectional illustrations of the gastrointestinal device of FIGS. 9A and 9B in respective open and closed positions.
Figure 9D:
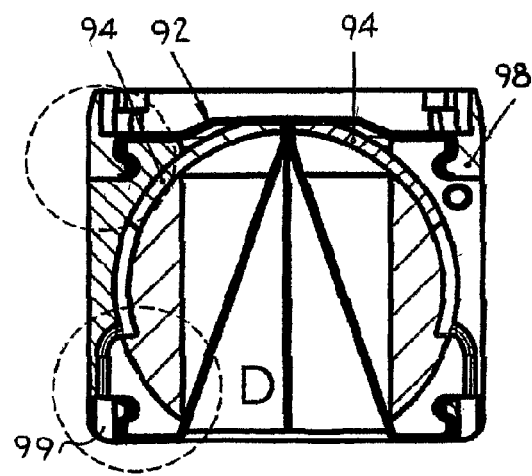

In FIG. 9C, shutters 94 are open, i.e., moved away from each other, and flexible sleeve 92 is also open so as to permit passage of fecal matter therepast. In FIG. 9D, shutters 94 are closed, i.e., moved towards each other (and may cross over each other), and flexible sleeve 92 is closed so as not to permit passage of fecal matter therepast.

Reference is now made to FIGS. 10A-10D, which illustrate a gastrointestinal device 100, constructed and operative in accordance with an embodiment of the present invention. Gastrointestinal device 100 may include a casing 101 that includes fixation elements (not shown for the sake of simplicity, but may be any of the fixation elements described herein) adapted for fixing the device 100 to the anorectal wall. Casing 101 may be constructed as a ring member (other structures are also possible), and may be closed at ends thereof by closure members 102 and 103.

The valve of gastrointestinal device 100 may include a flexible sleeve 104 held at ends thereof by closure members 102 and 103. Flexible sleeve 104 may be identical to flexible sleeve 92, described hereinabove.

Figure 10A:
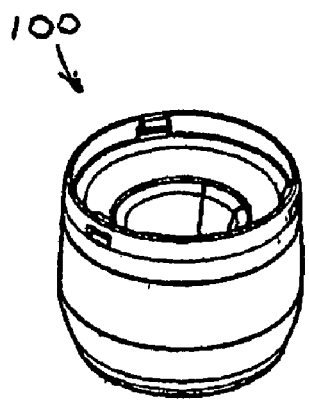
FIGS. 10A and 10B are simplified pictorial and exploded views, respectively, of a gastrointestinal device, constructed and operative in accordance with another embodiment of the present invention, including a flexible sleeve and an inflatable member.
Figure 10B:
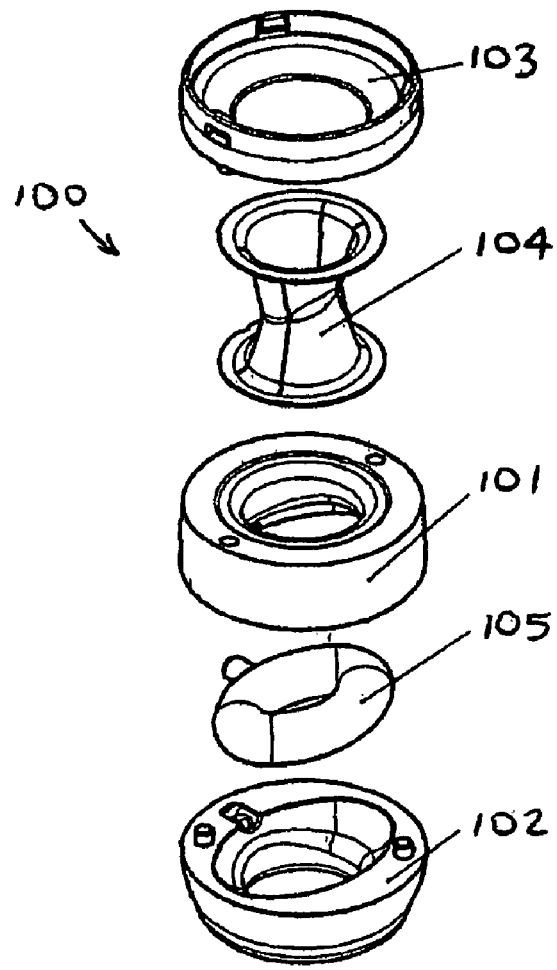
Figure 10D:
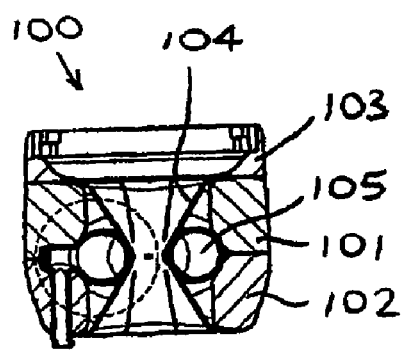
FIGS. 10C and 10D are simplified sectional illustrations of the gastrointestinal device of FIGS. 10A and 10B in respective open and closed positions.
Figure 10C:
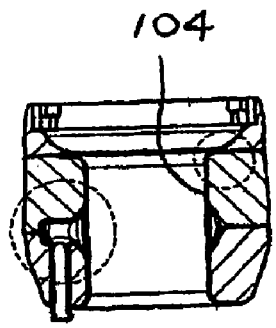
Figure 12A:
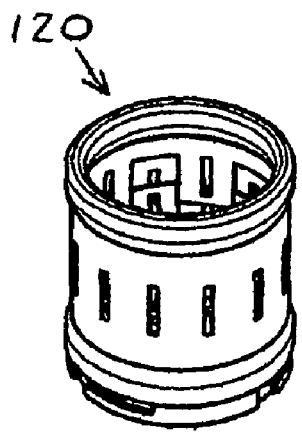
FIGS. 12A and 12B are simplified pictorial and exploded views, respectively, of a gastrointestinal device, constructed and operative in accordance with another embodiment of the present invention, with fixation elements that are barbs.
Figure 12B:
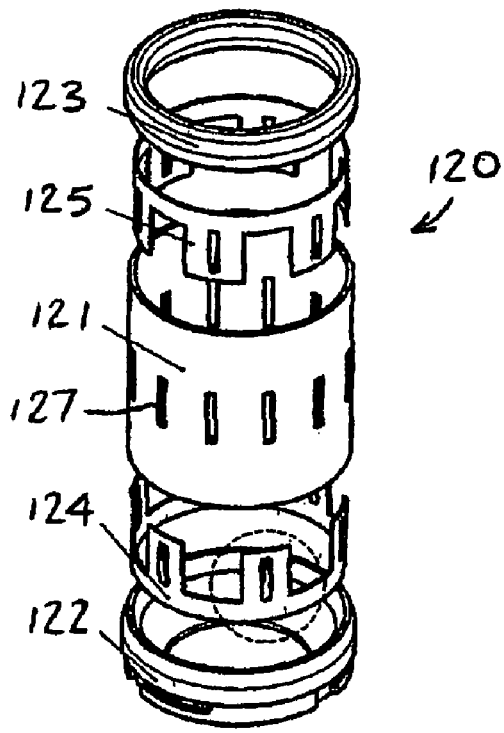
Figure 12C:
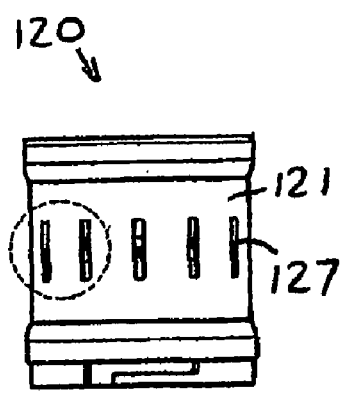
FIGS. 12C and 12D are simplified sectional illustrations of the gastrointestinal device of FIGS. 12A and 12B, before and after deployment, respectively.
Figure 12D:
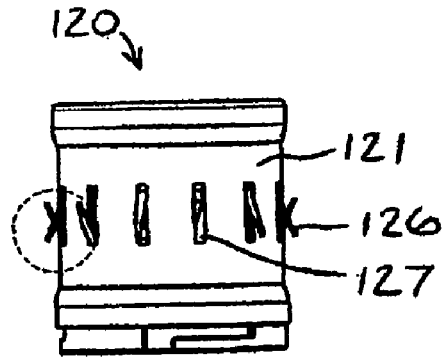

A controller may be provided that includes an inflatable member 105 (such as but not limited to, an inflatable balloon ring) positioned about flexible sleeve 104. Inflation of inflatable member 105 closes flexible sleeve 104, and deflation of inflatable member 105 opens flexible sleeve 104. For example, a fluid port 106 may be provided for connection to a fluid source (not shown, e.g., a source of pressurized water or air) to inflate inflatable member 105 and close flexible sleeve 104 (FIG. 10C) or deflate inflatable member 105 and open flexible sleeve 104 (FIG. 10D). It is noted that the valve may be configured to be opened with either positive (e.g., blowing) or negative pressure (e.g., sucking), and may be configured to, be closed with either positive or negative pressure.

Reference is now made to FIGS. 11A-11D, which illustrate a gastrointestinal device 110, constructed and operative in accordance with another embodiment of the present invention.

Gastrointestinal device 110 may include a casing 111 that includes fixation elements (not shown for the sake of simplicity, but may be any of the fixation elements described herein) adapted for fixing the device 110 to the anorectal wall. Casing 11 may be constructed as a ring member (other structures are also possible), and may be closed at ends thereof by closure members 112 and 113.

The valve of gastrointestinal device 100 may include a flexible sleeve 114 held at ends thereof by closure members 112 and 113. Flexible sleeve 114 may be identical to flexible sleeve 92, described hereinabove.

A controller may be provided that includes a fluid port 115 (which may be plugged by a plug 116) that may be connected to a fluid source (not shown, e.g., a source of pressurized water or air) to apply fluid pressure to close flexible sleeve 114 (FIG. 11C) or to apply fluid pressure to open flexible sleeve 114 (FIG. 11D). It is noted again that the valve may be opened with either positive or negative pressure, and may be closed with either positive or negative pressure.

In the embodiment of FIG. 1, the fixation elements 12 of gastrointestinal device 8 are rotatable hooks. Other fixation elements may also be employed, and one non-limiting example is now described with reference to FIGS. 12A-12D. Any of the gastrointestinal devices of the present invention may use these or other fixation elements.

In this embodiment, a casing 121 is provided, which may be cylindrical and closed at ends thereof by closure members 122 and 123. Fixation elements 124 and 125 may be disposed in casing 121 and sealed by closure members 122 and 123, respectively. Fixation elements 124 and 125 may include barbs 126 that can protrude through openings 127 formed in the peripheral wall of casing 121. In the position shown in FIG. 12C, the barbs 126 do not protrude through openings 127. In the position shown in FIG. 12D, fixation elements 124 and 125 have been moved (e.g., rotated, pulled or pushed, either manually or by some actuator) so that the barbs 126 now protrude through openings 127 and may fixedly grasp the anorectal wall.

The scope of the present invention includes both combinations and subcombinations of the features described hereinabove as well as modifications and variations thereof which would occur to a person of skill in the art upon reading the foregoing description and which are not in the prior art.

What is claimed is:

1. A gastrointestinal device comprising:
   a casing comprising fixation elements adapted for intraluminal fixation of the device in a gastrointestinal tract;
   a valve disposed in said casing and controllable to move from a closed position, which significantly restricts passage of gastrointestinal matter therepast, and an open position, which permits passage of gastrointestinal matter therepast; and
   a controller operatively connected to said valve for externally controlling the position of said valve between the closed and open positions, wherein distal extremities of said fixation elements, after entering tissue of said gastrointestinal tract, turn and point back towards an outer wall of said casing.

2. The gastrointestinal device according to claim 1, wherein said valve comprises a ball valve rotatable between the closed and open positions.

3. The gastrointestinal device according to claim 2, wherein said controller comprises at least one string attached to said ball valve, said at least one string, when pulled, causing said ball valve to rotate.

4. The gastrointestinal device according to claim 1, wherein said valve comprises a flexible sleeve which is deformable to be in the closed and open positions.

5. The gastrointestinal device according to claim 4, wherein said controller comprises shutters attached to said flexible sleeve, said shutters being selectively movable to cause said flexible sleeve to be in either of the closed and open positions.

6. The gastrointestinal device according to claim 5, wherein said shutters are actuated by fluid pressure, and said casing comprises a fluid port for connection to a fluid source to actuate said shutters.

7. The gastrointestinal device according to claim 4, wherein said controller comprises an inflatable member positioned about said flexible sleeve, wherein inflation of said inflatable member closes said flexible sleeve, and deflation of said inflatable member opens said flexible sleeve.

8. The gastrointestinal device according to claim 4, wherein said controller comprises a fluid inlet adapted to apply fluid pressure to said flexible sleeve, wherein application of a first fluid pressure closes said flexible sleeve, and application of a second fluid pressure opens said flexible sleeve.

9. The gastrointestinal device according to claim 1, wherein said fixation elements comprise rotatable hooks.

10. The gastrointestinal device according to claim 1, wherein said fixation elements comprise barbs.

11. The gastrointestinal device according to claim 1, further comprising an insertion assist device adapted to move said fixation elements to a fixed position in the gastrointestinal tract.

12. The gastrointestinal device according to claim 11, wherein said fixation elements comprise rotatable hooks, and wherein said insertion assist device comprises a trigger that actuates grabbers to rotate said rotatable hooks.

13. The gastrointestinal device according to claim 1, wherein said casing is formed with openings and wherein in the first position said fixation elements do not protrude through said openings and in the second position said fixation elements protrude through said openings.

14. The gastrointestinal device according to claim 1, wherein said fixation elements are movable between first and second positions, wherein in the first position said fixation elements do not protrude from said casing and in the second position said fixation elements protrude from said casing.

15. A gastrointestinal device comprising:
   a casing comprising fixation elements adapted for intraluminal fixation of the device in a gastrointestinal tract, said fixation elements comprising a plurality of hooks protruding outwards from an outer wall of said case, wherein distal extremities of said hooks are movable with respect to the outer wall of said casing, and wherein said distal extremities of said fixation elements, after entering tissue of said gastrointestinal tract, turn and point back towards the outer wall of said casing.

* * * * *